US010674941B2

(12) United States Patent
Tanaka et al.

(10) Patent No.: US 10,674,941 B2
(45) Date of Patent: Jun. 9, 2020

(54) MONITORING DEVICE, MONITORING SYSTEM, MONITORING METHOD, MONITORING PROGRAM, AND COMPUTER READABLE MEDIA WITH MONITORING PROGRAM RECORDING THEREON

(71) Applicant: OMRON Corporation, Kyoto-shi, Kyoto (JP)

(72) Inventors: Junichi Tanaka, Kyotanabe (JP); Fumiji Aita, Nara (JP)

(73) Assignee: OMRON Corporation, Kyoto-shi (JP)

( * ) Notice: Subject to any disclaimer, the term of this patent is extended or adjusted under 35 U.S.C. 154(b) by 220 days.

(21) Appl. No.: 15/114,034

(22) PCT Filed: Feb. 13, 2015

(86) PCT No.: PCT/JP2015/053928
§ 371 (c)(1),
(2) Date: Jul. 25, 2016

(87) PCT Pub. No.: WO2015/125701
PCT Pub. Date: Aug. 27, 2015

(65) Prior Publication Data
US 2017/0215770 A1 Aug. 3, 2017

(30) Foreign Application Priority Data

Feb. 21, 2014 (JP) .................... 2014-031444

(51) Int. Cl.
*A61B 5/11* (2006.01)
*G08B 21/04* (2006.01)
(Continued)

(52) U.S. Cl.
CPC .......... *A61B 5/1117* (2013.01); *A61B 5/0059* (2013.01); *A61B 5/0075* (2013.01);
(Continued)

(58) Field of Classification Search
CPC ... A61B 5/1128; A61B 5/1115; A61B 5/1117; A61B 5/1123; A61B 2562/046
See application file for complete search history.

(56) References Cited

U.S. PATENT DOCUMENTS 9,538,158 B1 * 1/2017 Rush ................. A61B 5/002
2008/0021731 A1 1/2008 Rodgers
(Continued)

FOREIGN PATENT DOCUMENTS

CN 103221984 A 7/2013
EP 2589330 A1 5/2013
(Continued)

OTHER PUBLICATIONS

Extended European search report (EESR) dated Jul. 6, 2017 in a counterpart European patent application.
(Continued)

*Primary Examiner* — Patrick Fernandes
(74) *Attorney, Agent, or Firm* — Metrolex IP Law Group, PLLC

(57) ABSTRACT

A position identifying unit is configured to identify the location of a monitored person in the horizontal direction and maximum height of the monitored person in the vertical direction on the basis of top-down image data acquired by an upper image sensor provided above a monitored area capturing an image of the monitored area and lateral image data acquired by a lateral image sensor provided along a side of the monitored area capturing an image of the monitored area. An event determining unit assesses a fall-related event for the monitored person on the basis of a location in the horizontal direction, a maximum height in the vertical direction.

10 Claims, 21 Drawing Sheets

(51) Int. Cl.
  *A61B 5/00* (2006.01)
  *G06K 9/00* (2006.01)
  *G06T 7/254* (2017.01)
  *H04N 7/18* (2006.01)

(52) U.S. Cl.
  CPC .......... *A61B 5/0077* (2013.01); *A61B 5/1115* (2013.01); *A61B 5/1128* (2013.01); *A61B 5/6889* (2013.01); *A61B 5/7282* (2013.01); *G06K 9/00771* (2013.01); *G06T 7/254* (2017.01); *G08B 21/043* (2013.01); *G08B 21/0476* (2013.01); *A61B 2503/08* (2013.01); *A61B 2576/00* (2013.01); *G06T 2207/30196* (2013.01); *G06T 2207/30232* (2013.01); *H04N 7/18* (2013.01)

(56) References Cited

U.S. PATENT DOCUMENTS

| | | |
|---|---|---|
| 2009/0044334 A1 | 2/2009 | Parsell et al. |
| 2012/0075464 A1* | 3/2012 | Derenne .............. A61B 5/0013 348/135 |
| 2013/0242074 A1 | 9/2013 | Sekiguchi et al. |

FOREIGN PATENT DOCUMENTS

| | | |
|---|---|---|
| JP | 2000-253382 A | 9/2000 |
| JP | 2000-285223 A | 10/2000 |
| JP | 2001-307246 A | 11/2001 |
| JP | 2002-373388 A | 12/2002 |
| JP | 2004-96457 A | 3/2004 |
| JP | 2011-86286 A | 4/2011 |

OTHER PUBLICATIONS

Japanese Office Action (JPOA) dated Feb. 20, 2018 in a counterpart Japanese patent application.

* cited by examiner

Regions Labeled "1"

MONITORING DEVICE, MONITORING SYSTEM, MONITORING METHOD, MONITORING PROGRAM, AND COMPUTER READABLE MEDIA WITH MONITORING PROGRAM RECORDING THEREON

FIELD

The present invention relates to a monitoring device, a monitoring system, a monitoring method, a monitoring program, and a computer readable media with monitoring program recording thereon.

BACKGROUND

There is technology available for automatically detecting an abnormal state in a room occupant, particularly a person who requires care, such as an elderly person. For instance, the fall detector in Japanese Unexamined Patent Application Publication No. 2000-285223 (Patent Document 1) is provided with a sidewall camera that captures an image of the room's occupant from the side, and a ceiling camera that captures an image of the room's occupant from above. An image processing unit uses the images captured by the cameras to calculate the distance from the occupant to the sidewall camera, as well as to calculate the occupant's height. A height correction unit makes corrections to the height calculated taking into account the error generated due to the difference in the distance from the occupant to the sidewall camera. A determination unit detects the occupant's falling motion on the basis of changes per unit time in the occupant's height information obtained from correcting the occupant's height.

RELATED ART DOCUMENTS

Patent Documents

Patent Document 1: Japanese Unexamined Patent Application Publication No. 2000-285223

SUMMARY

Technical Problem

Unfortunately, based on the change per unit time of the occupant's height information, the device described in Patent Document 1 also tends to determine that the occupant has fallen when the occupant is sleeping on a bed.

What is desired is the capability to not only detect when the occupant has actually fallen, but to also detect situations where the occupant is likely to fall. Knowing of the risk of falling in advance makes it possible to prevent the occupant from falling.

Consequently, embodiments of the invention propose a monitoring device capable of detecting the fall-related events for a person being monitored, i.e., detecting the state or the likelihood of a fall, even when the area being monitored contains a bed; embodiments of the invention also provide a monitoring system, a monitoring method, a monitoring program, and a computer readable media with monitoring program recording thereon capable of the same.

Solution to Problem

A monitoring device according to embodiments of the invention is provided with a position identifying unit configured to identify the location of a monitored person in the horizontal direction and maximum height of the monitored person in the vertical direction on the basis of top-down image data acquired by a first image sensor provided above a monitored area capturing an image of the monitored area and lateral image data acquired by a second image sensor provided along a side of the monitored area capturing an image of the monitored area; and an event determining unit configured to assess a fall-related event for the monitored person on the basis of the location in the horizontal direction and the maximum height in the vertical direction.

The event determining unit may be configured to determine that the monitored person is lying down when the monitored person is located in a first region in the horizontal direction, and the maximum height of the monitored person in the vertical direction is less than or equal to a first predetermined value.

The event determining unit may be configured to determine that the monitored person is sitting legs outstretched when the monitored person is located in the first region in the horizontal direction, and the maximum height of the monitored person in the vertical direction exceeds the first predetermined value.

The event determining unit may be configured to determine that the monitored person is sitting square when the monitored person is located in a second region that surrounds the first region in the horizontal direction, and the maximum height of the monitored person in the vertical direction is greater than or equal to a first predetermined value.

The monitored area may be a space where the monitored person resides, and the first region may contain a bed.

The position identifying unit may use the top-down image data to calculate the length of the monitored person in the horizontal direction. Further, the event determining unit may determine that the monitored person has fallen from the bed when the monitored person is located in the second region, the maximum height of the monitored person in the vertical direction is less than or equal to the first predetermined value, and the length of the monitored person in the horizontal direction is greater than or equal to a second predetermined value.

The event determining unit may determine that the monitored person has experienced a fall event when the monitored person is located in a third region that excludes the first region and the second region in the horizontal direction, and the maximum height of the monitored person in the vertical direction is less than or equal to the first predetermined value.

The event determining unit may determine that the monitored person is standing when the monitored person is located in the third region in the horizontal direction, and the maximum height of the monitored person in the vertical direction exceeds the first predetermined value.

The position identifying unit may identify the minimum height of the monitored person in the vertical direction on the basis of the lateral image data. The event determining unit may determine that the monitored person is in an area containing a bed when the minimum height of the monitored person in the vertical direction is greater than or equal to a third predetermined value.

The position identifying unit may be configured to use the top-down image data acquired by the first image sensor capturing an image of the monitored area to identify the number of persons in the monitored area, and to only identify the location of the monitored person in the horizontal direction and the maximum height of the monitored person in the vertical direction on determining that there is only one person in the monitored area.

A monitoring system according to embodiments of the invention is provided with a first image sensor provided above a monitored area; a second image sensor provided along a side of the monitored area; a position identifying unit configured to identify the location of a monitored person in the horizontal direction and the maximum height of the monitored person in the vertical direction on the basis of top-down image data acquired by the first image sensor capturing an image of the monitored area and lateral image data acquired by the second image sensor capturing an image of the monitored area; and an event determining unit configured to assess a fall-related event for the monitored person on the basis of the location in the horizontal direction and the maximum height in the vertical direction.

A monitoring method includes steps of identifying the location of a monitored person in the horizontal direction and maximum height of the monitored person in the vertical direction on the basis of top-down image data acquired by a first image sensor provided above a monitored area capturing an image of the monitored area and lateral image data acquired by a second image sensor provided along a side of the monitored area capturing an image of the monitored area; and assessing a fall-related event for the monitored person on the basis of the location in the horizontal direction and the maximum height in the vertical direction.

A monitoring program according to embodiments of the invention causes a computer to serve as a position identifying unit configured to identify the location of a monitored person in the horizontal direction and maximum height of the monitored person in the vertical direction on the basis of top-down image data acquired by a first image sensor provided above a monitored area capturing an image of the monitored area and lateral image data acquired by a second image sensor provided along a side of the monitored area capturing an image of the monitored area; and an event determining unit configured to determine a fall-related event for the monitored person on the basis of the location in the horizontal direction and the maximum height in the vertical direction.

A monitoring program according to embodiments of the invention is recorded on a computer readable medium. The monitoring program causes a computer to serve as a position identifying unit configured to identify the location of a monitored person in the horizontal direction and maximum height of the monitored person in the vertical direction on the basis of top-down image data acquired by a first image sensor provided above a monitored area capturing an image of the monitored area and lateral image data acquired by a second image sensor provided along a side of the monitored area capturing an image of the monitored area; and an event determining unit configured to determine a fall-related event for the monitored person on the basis of the location in the horizontal direction and the maximum height in the vertical direction.

Effects

Embodiments of the invention are capable of detecting the state of fall of a person being monitored even with a bed located in the area being monitored.

DETAILED DESCRIPTION

Embodiments of the present invention are described in detail below with reference to the drawings.

First Embodiment

In the description that follows, a "monitored person" refers to an occupant of the environment requiring care, such as an elderly person, and a "monitored area" refers to a space occupied by the monitored person.

Figure 1:
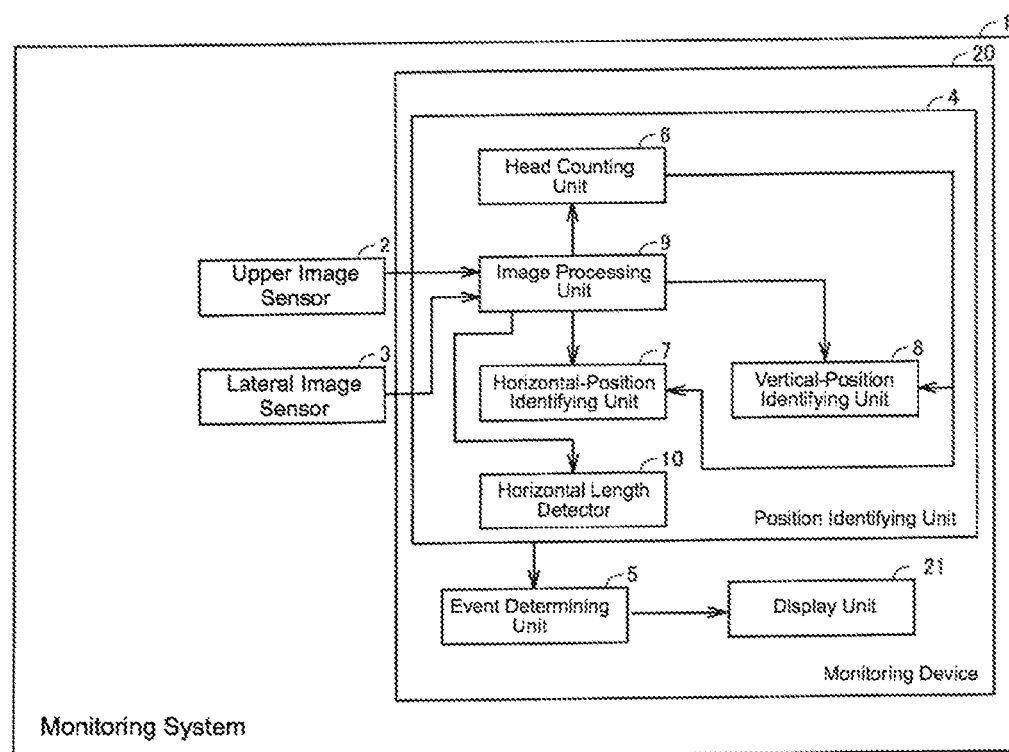
FIG. 1 illustrates a configuration of a monitoring system according to a first embodiment.

FIG. 1 illustrates a configuration of a monitoring system according to a first embodiment.

As illustrated in FIG. 1 a monitoring system 1 is provided with an upper image sensor 2, a lateral image sensor 3, and a monitoring device 20. The monitoring device 20 is provided with a position identifying unit 4, an event determining unit 5, and a display unit 21.

The position identifying unit 4, and the event determining unit 5 may be implemented on a computer (not shown) executing a monitoring program. In other words, a monitoring program may cause a computer to function as a position identifying unit 4 and an event determining unit 5. The monitoring program may be stored in a computer readable medium such as a memory card, a CD-ROM, or a DVD, and then installed on a computer.

The position identifying unit 4 includes an image processing unit 9, a head counting unit 6, a horizontal-position identifying unit 7, a vertical-position identifying unit 8, and a horizontal length detector 10.

The upper image sensor 2 captures an image of the monitored area from above. The lateral image sensor 3 captures an image of the monitored area from the side. In the embodiment, the upper image sensor 2 and the lateral image sensor 3 are described as being configured by infrared sensor arrays; however, these sensors may also be configured from other types of sensors such as visible light cameras.

The first infrared image data output from the upper image sensor 2 is sent to the image processing unit 9. The second infrared image data output from the lateral image sensor 3 is sent to the image processing unit 9.

Infrared image data is characterized by having a number of pixels proportional to the temperature of the region captured so that the higher the temperature of the region captured, the higher the number of pixels, and the lower the temperature of the region captured, the lower the number of pixels. Given that the temperature is high in the region where a person is present, the number of pixels in a region capturing an image of a person is also high. Accordingly, it is possible to identify where a person is present by finding the region that has a high number of pixels in the infrared image data.

Figure 2:
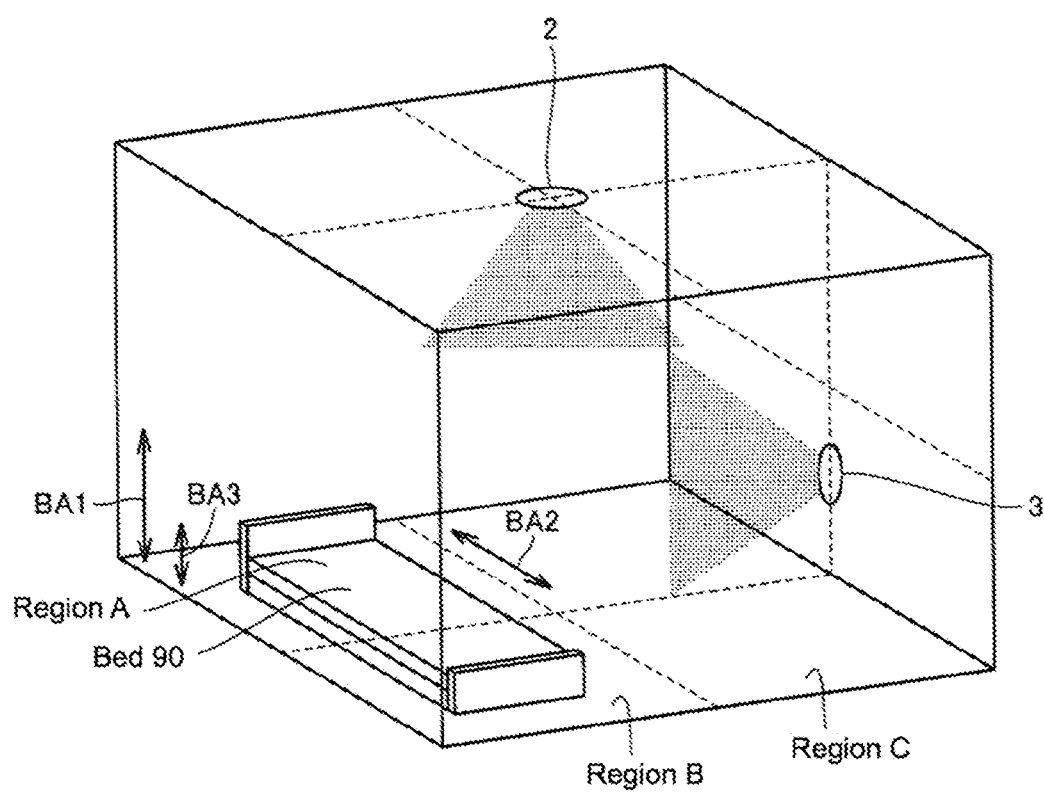
FIG. 2 is a three-dimensional diagram of a monitored area.

FIG. 2 is a three-dimensional diagram of a monitored area.

As illustrated in FIG. 2, the upper image sensor 2 is installed above the monitored area, and the lateral image sensor 3 is installed along a side of the monitored area.

A bed 90 is provided in the monitored area. Assume the bed is present in Region A, and that the region surrounding the bed 90 is Region B. For instance, assume that Region B is an area of up to 50 cm beyond the edge of the bed 90. Within the monitored area, Region C indicates a region not including Region A and Region B.

A reference value BA1 is established for the vertical direction, primarily for determining whether or not the monitored person has fallen in Region C. The monitored person is determined to have fallen if the maximum height of the monitored person's body is less than or equal to the reference value BA1. In the later-described second embodiment, a reference value BA3 in the vertical direction is established to determine whether or not the monitored person is present in the area including the bed. A reference value BA2 is also established in the horizontal direction to determine whether or not the monitored person has experienced one kind of fall in Region B, i.e., falling from the bed. The monitored person is determined to have fallen if the length of the monitored person in the horizontal direction is greater than or equal to the reference value BA2.

Figure 4:
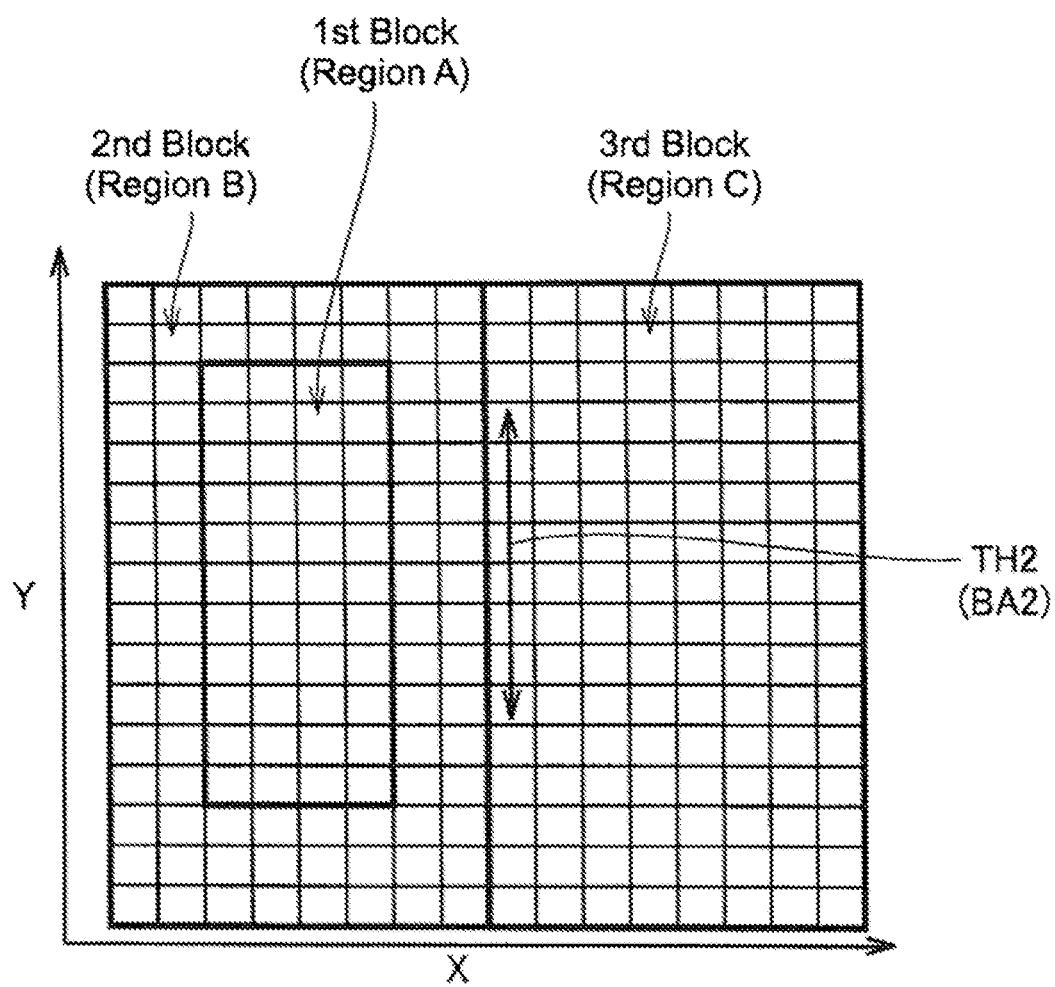
FIG. 4 is for describing a first infrared image.

FIG. 4 is for describing a first infrared image. The first infrared image is made up of 16 pixels in the X direction and 16 pixels in the Y direction.

Assume that "first block", "second block", and "third block" indicate the portions of the image capturing Region A, Region B, and Region C respectively.

A predetermined distance TH2 between the pixels in the first infrared image represents the reference value BA2 in the monitored area.

Figure 3:
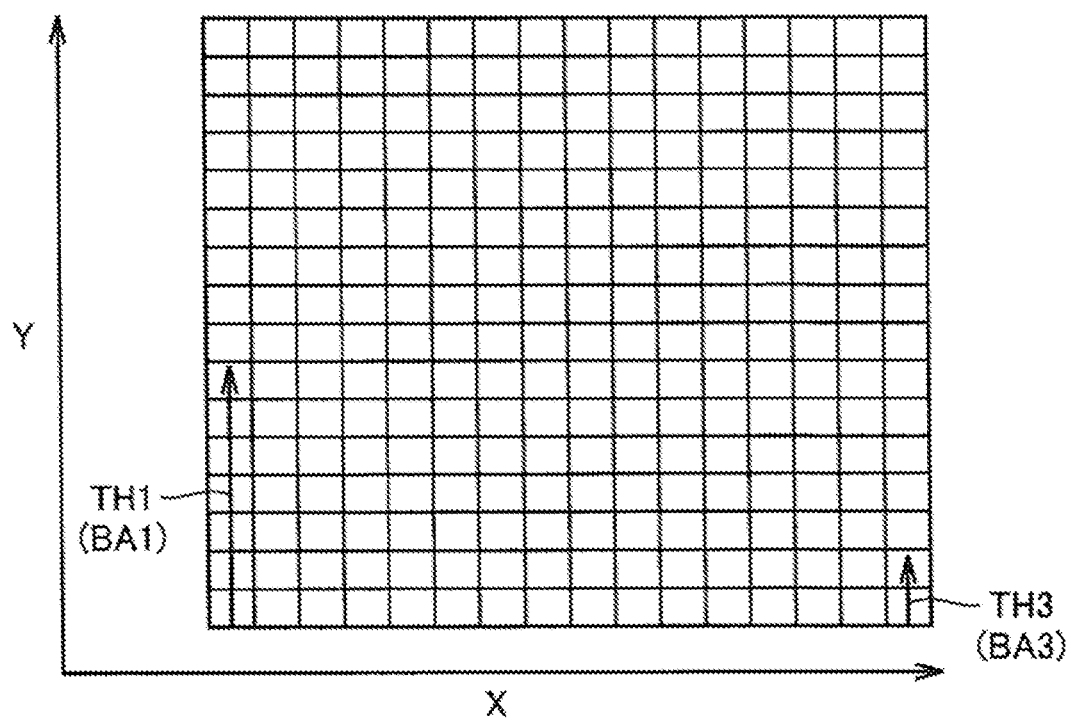
FIG. 3 is for describing a second infrared image.

FIG. 3 is for describing a second infrared image. The second infrared image is made up of 16 pixels in the X direction and 16 pixels in the Y direction. A predetermined Y coordinate TH1 in the second infrared image represents the reference value BA1 in the monitored area. A predetermined Y coordinate TH3 in the second infrared image represents the reference value BA3 in the monitored area.

Figure 5:
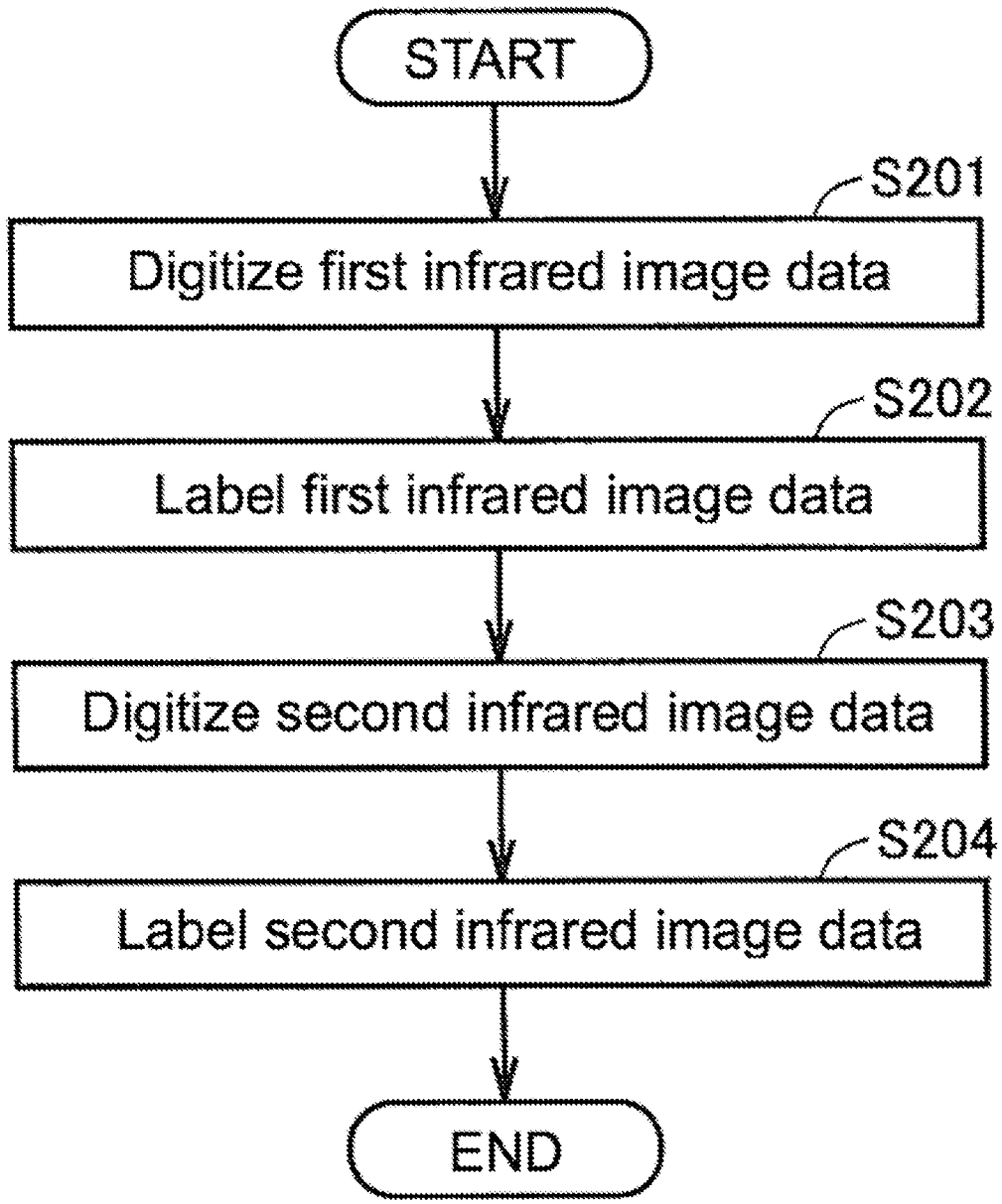
FIG. 5 is a flowchart of the procedures in the image processing unit.

FIG. 5 is a flowchart of the procedures in the image processing unit 9.

In step S201 the image processing unit 9 setting the value of pixels included in the first infrared image data output from the upper image sensor 2 to "1" if the pixel is above a predetermined value, and to "0" if the pixel is below a predetermined value to thereby generate first binary infrared image data.

In step S202, the image processing unit 9 then labels pixels in region where a person is present with the value "1" and labels pixels in a region where no person is present with the value "0" to thereby generate a first labeled image data from the first binary infrared image data. In other words, the image processing unit 9 labels the pixels in a region of uninterrupted pixels with "1", when the pixels labeled with "1" in the first binary infrared image data are continuous, and that region of uninterrupted pixels is greater than or equal to a fixed size (i.e., the number of pixels is less than or equal to a predetermined value). The image processing unit 9 further labels the pixels in a region of uninterrupted pixels with "0", when the pixels labeled with "1" in the first binary infrared image data are continuous, but the region of uninterrupted pixels is less than to a fixed size (i.e., the number of pixels is greater than or equal to a predetermined value). Furthermore, the image processing unit 9 labels a pixel in the first binary infrared image data having the value "1" with a value of "0" when no pixel with the value "1" is next to the pixel with the value "1". That is, the image processing unit 9 labels a pixel in the first binary infrared image data having a value of "0" with a value of "0".

In step S203 the image processing unit 9 sets the value of pixels included in the second infrared image data output from the lateral image sensor 3 to "1" when the pixel value is above a predetermined value, and to "0" when the pixel value is below a predetermined value to thereby generate second binary image data.

In step S204, the image processing unit 9 then generates second labeled image data from the second binary infrared image data in the same manner as step S202, by labeling a region where a person is present with a pixel value of "1", and labeling a region where no person is present with a pixel value of "0".

The head counting unit 6 determines the number of persons within the monitored area on the basis of the first labeled image data.

The horizontal-position identifying unit 7 determines the location of the horizontal center of gravity of the monitored person on the basis of the first labeled image data.

The vertical-position identifying unit 8 determines the maximum height of the monitored person on the basis of the first labeled image data and the second labeled image data.

The horizontal length detector 10 detects the horizontal length of the monitored person on the basis of the first labeled image data.

The event determining unit 5 assesses the kind of fall event of the monitored person on the basis of the location of the horizontal center of gravity of the monitored person, the maximum height of the monitored person, and the horizontal length of the monitored person. Here, "to fall" includes falling over because of tripping or stumbling while walking, and falling off a bed.

In addition to the falling motion, the event determining unit 5 also assesses states of standing, sitting in bed (hereafter, sitting legs outstretched), and sitting on the edge of the bed (hereafter, sitting square). Determining these other state is necessary, particularly because, if the monitored person has trouble walking, then when sitting legs outstretched or sitting square, the monitored person may soon stand up but then fall over, and thus attention is needed.

The display unit 21 presents the results of the assessment by the event determining unit 5. When a fall event is shown on the display unit 21, for instance, the person in charge of monitoring the monitored person can rush to monitored area to aid the monitored person. When the display unit 21 shows the monitored person sitting legs outstretched, or sitting square, for instance, the person in charge of monitoring the monitored person can rush to the monitored area to aid the monitored person.

Figure 6:
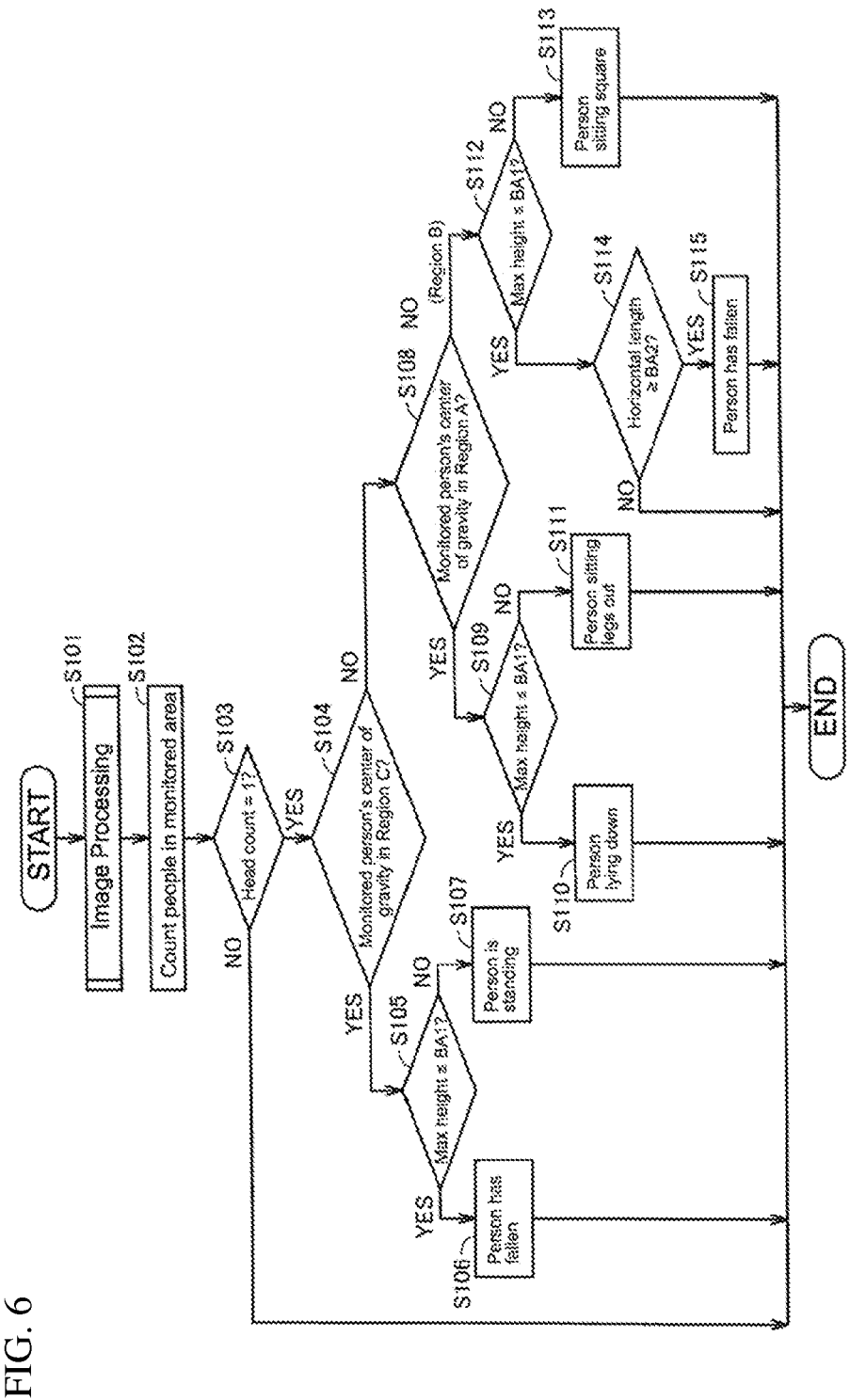
FIG. 6 is a flowchart of the procedures for assessing events surrounding a monitored person according to the first embodiment.

FIG. 6 is a flowchart of the procedures for assessing events surrounding a monitored person according to the first embodiment.

In step S101, the image processing unit 9 performs image processing according to the procedure depicted in FIG. 5 and thereby generates a first labeled image data and a second labeled image data from the first infrared image data output from the upper image sensor 2 and the second infrared image data output from the lateral image sensor 3.

In step S102, the head counting unit 6 identifies the number of people in the monitored area on the basis of the number of uninterrupted regions labeled with "1" in the first labeled image data. The head counting unit 6 determined there are N people in the monitored area when N uninterrupted regions in the first labeled image data are labeled with "1".

In step S103, the head counting unit 6 determines that only the monitored person is in the monitored area when only one person is present in the monitored area, and processing continues to step S104. When multiple people are in the monitored area, the head counting unit 6 determines that other persons are present in the monitored area besides the monitored person, e.g., an assistant or the like, and that monitoring by the monitoring system 1 is unnecessary, and thus processing terminates.

In step S104, the horizontal-position identifying unit 7 determines the horizontal location of the center of gravity of the monitored person's physical body on the basis of the first labeled image data. The horizontal-position identifying unit 7 determines whether or not the center of gravity of the monitored person's physical body is within Region C (FIG. 2; i.e., the region excluding the bed and the region surrounding the bed). That is, the horizontal-position identifying unit 7 determines that the center of gravity of the monitored person is in Region C when the pixels at the center of gravity of the region labeled with "1" in the first labeled image data are included in the third block (FIG. 4) corresponding to Region C. The horizontal-position identifying unit 7 determines that the center of gravity of the monitored person is not within Region C when the pixels at the center of gravity of the region labeled with "1" within the first labeled image data to indicate the monitored person is not included in the third block (FIG. 4) corresponding to Region C. Processing continues to step S105 when the horizontal-position identifying unit 7 determines that the monitored person is within the region C, and continues to step S108 when the horizontal-position identifying unit 7 determines that the monitored person is not within the region C.

In step S105, the vertical-position identifying unit 8 determines whether or not the maximum height of the physical body of the monitored person is less than or equal to the reference value BA1 (FIG. 2) on the basis of the second labeled image data. In other words, the vertical-position identifying unit 8 corrects the regions labeled with "1" within the second labeled image data on the basis of the location of the pixels at the center of gravity of the monitored person's physical body identified in step S104. This is because the closer the monitored person is to the lateral image sensor 3, the larger the Y coordinate in the region the monitored person present; therefore, the correction is needed to ensure that the Y coordinate is uniform wherever the monitored person is located in the horizontal direction. The vertical-position identifying unit 8 identifies the maximum Y coordinate of the pixels corrected in the regions labeled with "1" in the second labeled image data. When the vertical-position identifying unit 8 determines that the identified maximum Y coordinate YMAX is less than or equal to a predetermined value TH1 (FIG. 3) corresponding to the reference value BA1, processing continues to step S106. Processing continues to step S107 when the vertical-position identifying unit 8 determines that the identified maximum Y coordinate YMAX exceeds the predetermined value TH1.

In step S106 the event determining unit 5 determines that the monitored person has fallen.

Figure 7:
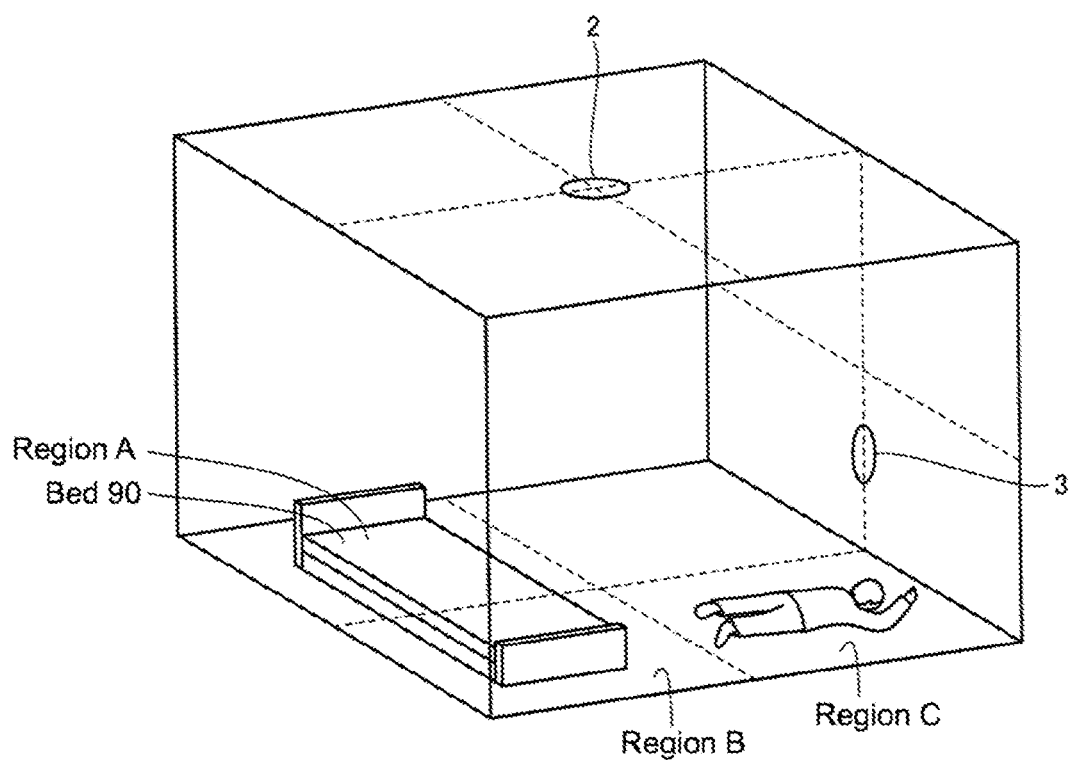
FIG. 7 illustrates the state of the monitored area when a monitored person has fallen.
Figure 8:
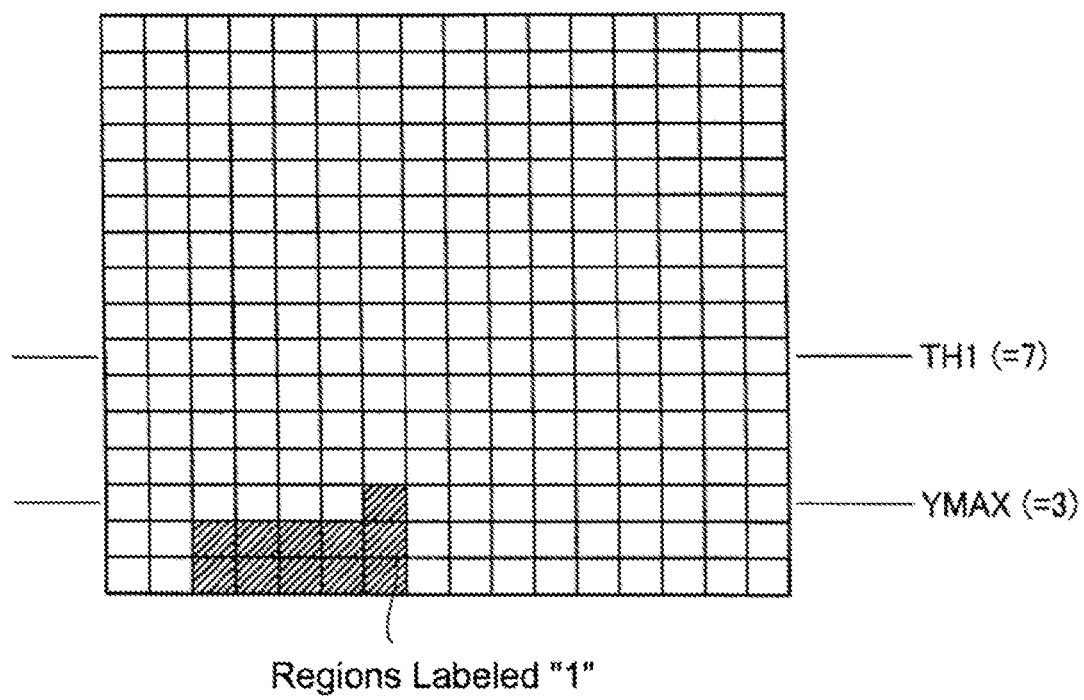
FIG. 8 depicts second labeled image data when the monitored area is in the state illustrated in FIG. 7.

FIG. 7 illustrates the state of the monitored area when a monitored person has fallen. FIG. 8 depicts second labeled image data when the monitored area is in the state illustrated in FIG. 7. The maximum Y coordinate among the pixels in the region labeled "1" in the second labeled image data is "3". Given that the predetermined value TH1 is given the value "7", the system determines that the monitored person has fallen.

In step S107 the event determining unit 5 determines that the monitored person is standing.

Figure 9:
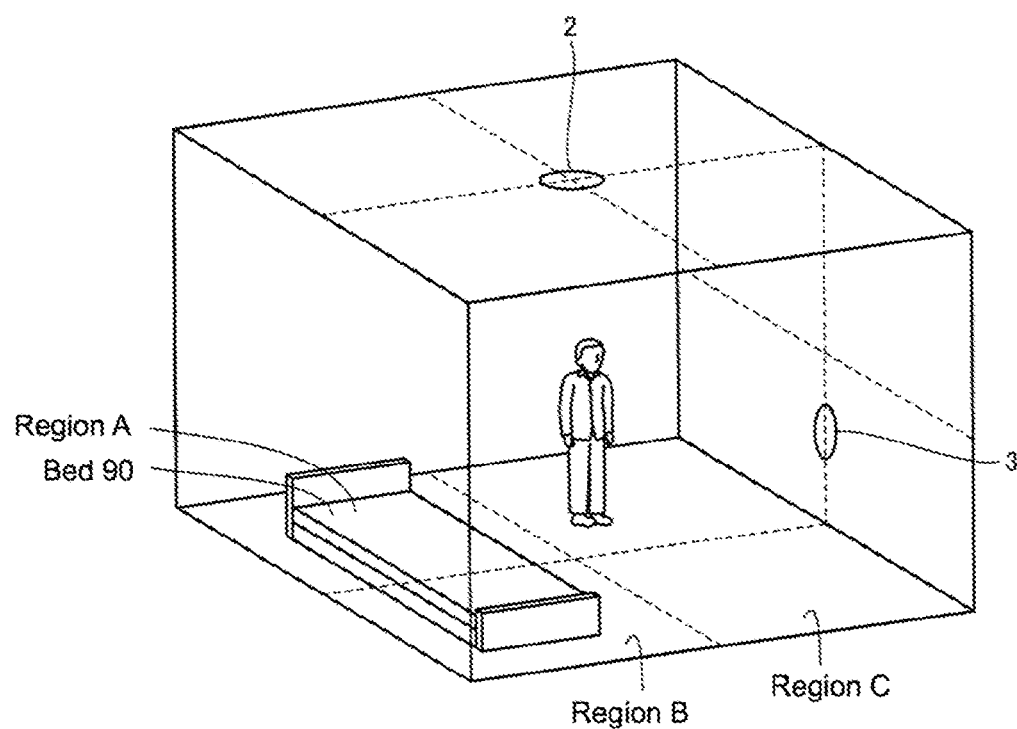
FIG. 9 illustrates the state of the monitored area when a monitored person is standing.
Figure 10:
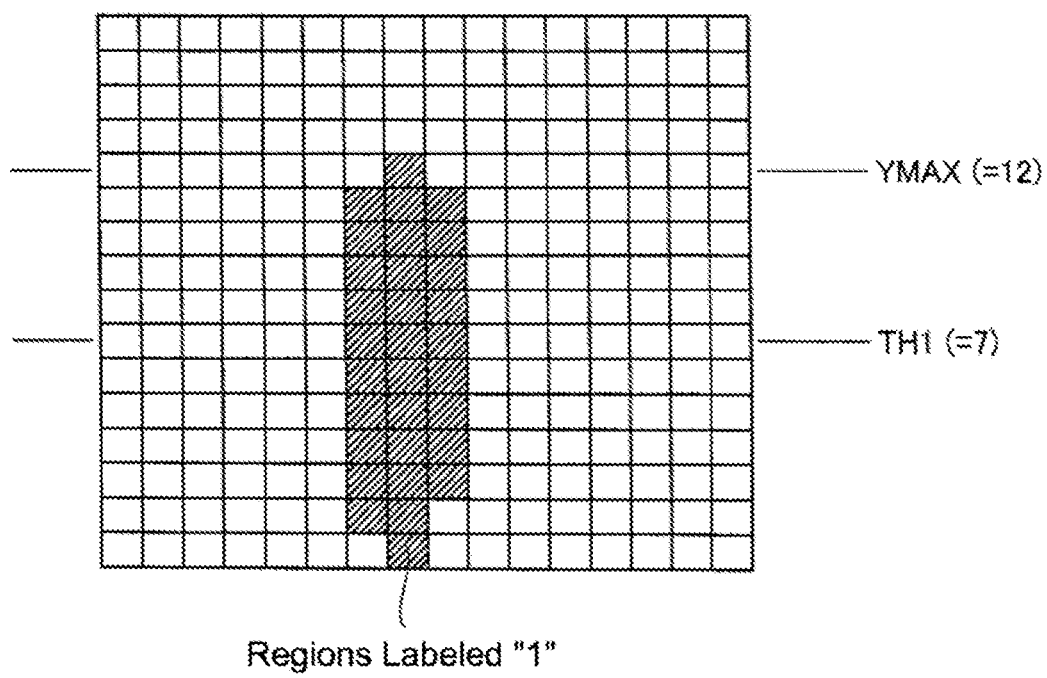
FIG. 10 illustrates a second labeled image data when the monitored area is in the state illustrated in FIG. 9.

FIG. 9 illustrates the state of the monitored area when a monitored person is standing. FIG. 10 illustrates a second labeling of image data when the monitored area is in the state illustrated in FIG. 9. The maximum Y coordinate among the pixels in the region labeled "1" in the second labeled image data is "12". Given that the predetermined value TH1 is given the value "7", the system determines that the monitored person is standing.

In step S108, the horizontal-position identifying unit 7 determines the horizontal location of the center of gravity of the monitored person's physical body on the basis of the first labeled image data. The horizontal-position identifying unit 7 determines whether or not the center of gravity of the monitored persons physical body is within Region A (FIG. 2; i.e., the bed area). That is, the horizontal-position identifying unit 7 determines that the center of gravity of the monitored person is included in Region A when the pixels at the center of gravity of the region labeled with "1" in the first labeled image data to indicate the monitored person is included in the first block corresponding to Region A (FIG. 3); and, determines that the center of gravity of the monitored person is not included in Region A when the pixels at the center of gravity of the region labeled with "1" in the first labeled image data is not included in the first block (FIG. 3). Processing continues to step S109 when the horizontal-position identifying unit 7 determines that the monitored person is in Region A, and continues to step S112 when the horizontal-position identifying unit 7 determines that the monitored person is not in Region A.

In step S109, the vertical-position identifying unit 8 determines whether or not the maximum height the physical body of the monitored person is less than or equal to the reference value BA1 (FIG. 2) on the basis of the second labeled image data. In other words, the vertical-position identifying unit 8 corrects the region labeled with "1" in the second labeled image data on the basis of the location of the center of gravity of the pixels of the monitored person's body identified in step S108. The vertical-position identifying unit 8 identifies the maximum Y coordinate of the pixels corrected in the regions labeled with "1" in the second labeled image data. When the vertical-position identifying unit 8 determines that the identified maximum Y coordinate YMAX is less than or equal to a predetermined value TH1 (FIG. 3) corresponding to the reference value BA1, processing continues to step S110. Processing continues to step S111 when the vertical-position identifying unit 8 determines that the identified maximum Y coordinate YMAX exceeds the predetermined value TH1.

In step S110 the event determining unit 5 determines that the monitored person is lying down.

Figure 11:
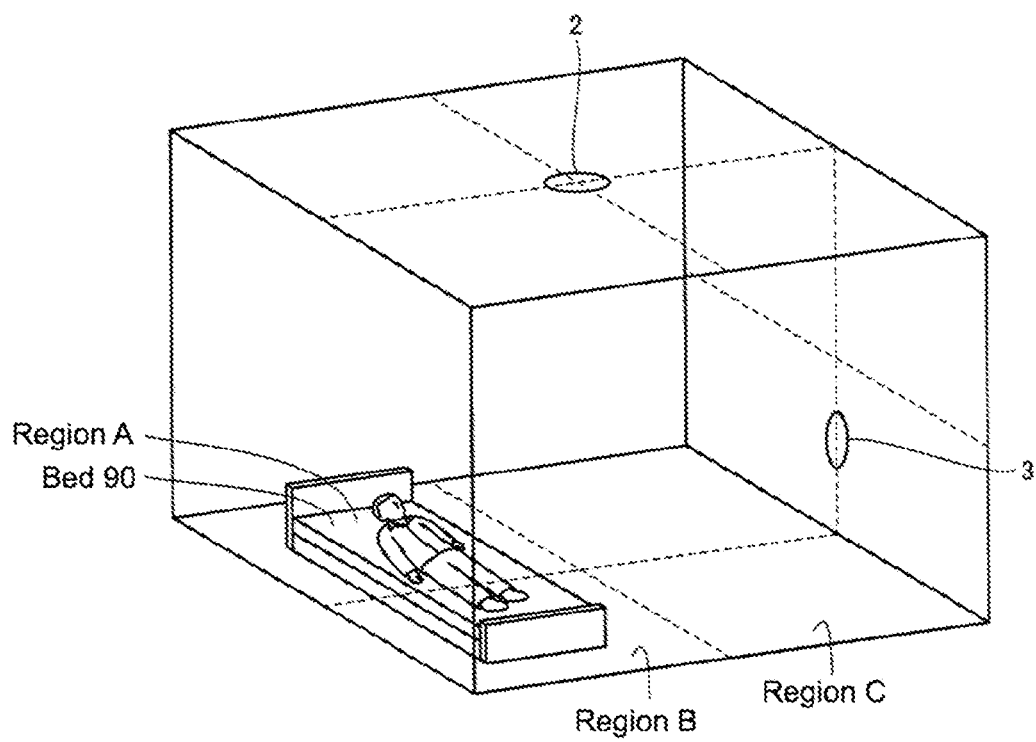
FIG. 11 illustrates the state of the monitored area when a monitored person is lying down.
Figure 12:
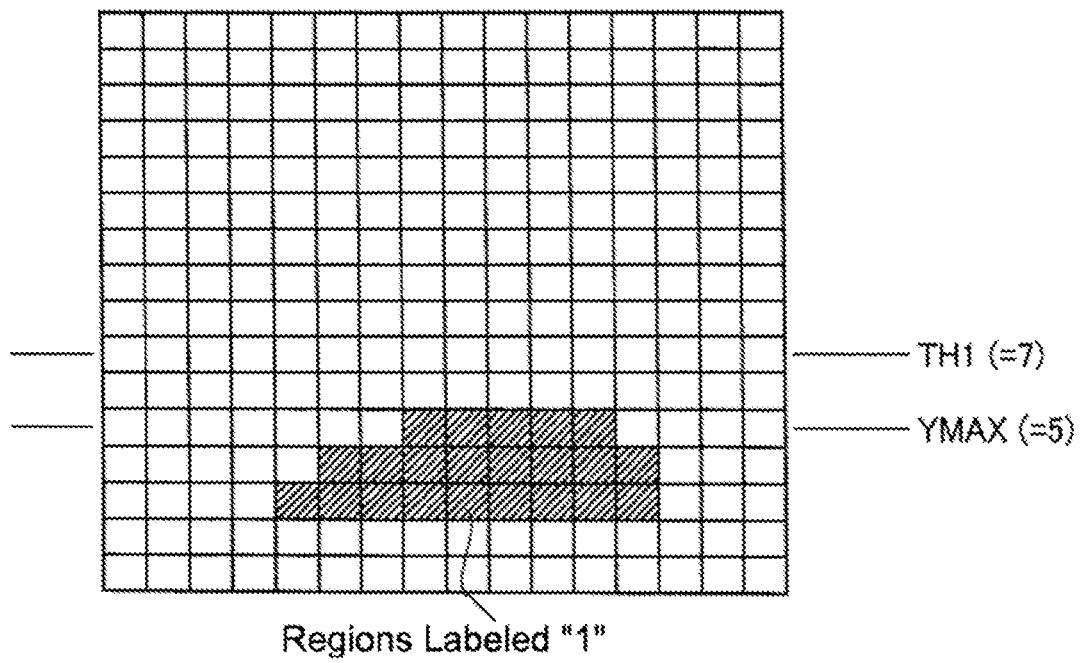
FIG. 12 illustrates a second labeled image data when the monitored area is in the state illustrated in FIG. 11.

FIG. 11 illustrates the state of the monitored area when a monitored person is lying down. FIG. 12 illustrates a second labeled image data when the monitored area is in the state illustrated in FIG. 11. The maximum Y coordinate among the pixels in the region labeled "1" in the second labeled image data is "5". Given that the predetermined value TH1 is given the value "7", the system determines that the monitored person is lying down.

In step S111 the event determining unit 5 determines that the monitored person is sitting with legs outstretched.

Figure 13:
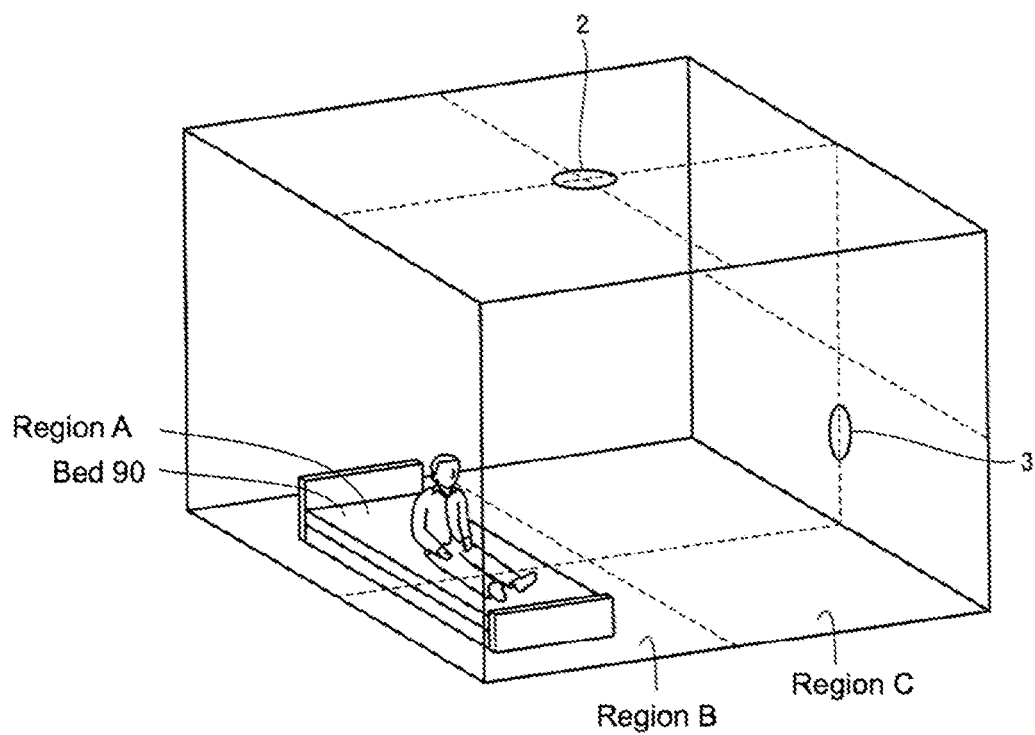
FIG. 13 illustrates the state of the monitored area when a monitored person is sitting long.
Figure 14:
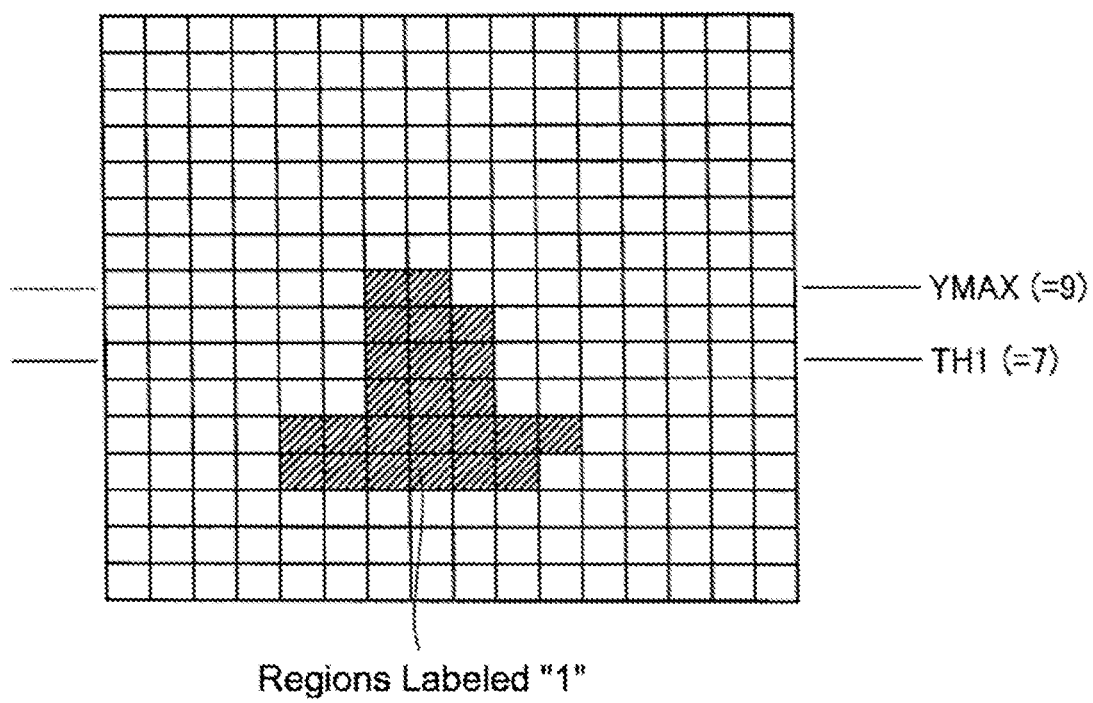
FIG. 14 illustrates a second labeled image data when the monitored area is in the state illustrated in FIG. 13.

FIG. 13 illustrates the state of the monitored area when a monitored person is sitting with legs outstretched. FIG. 14 illustrates a second labeled image data when the monitored area is in the state illustrated in FIG. 13. The maximum Y coordinate among the pixels in the region labeled "1" in the second labeled image data is "9". Given that the predetermined value TH1 is given the value "7", the system determines that the monitored person is sitting with legs outstretched.

In step S112, the vertical-position identifying unit 8 determines whether or not the maximum height of the physical body of the monitored person is less than or equal to the reference value BA1 (FIG. 2) on the basis of the second labeled image data. In other words, the vertical-position identifying unit 8 corrects the region labeled with "1" in the second labeled image data on the basis of the location of the center of gravity of the pixels of the monitored person's body identified in step S108. The vertical-position identifying unit 8 identifies the maximum Y coordinate of the pixels corrected in the regions labeled with "1" in the second labeled image data. When the vertical-position identifying unit 8 determines that the identified maximum Y coordinate YMAX is less than or equal to a predetermined value TH1 (FIG. 3) corresponding to the reference value BA1, processing continues to step S114. Processing continues to step S113 when the vertical-position identifying unit 8 determines that the identified maximum Y coordinate YMAX exceeds the predetermined value TH1.

In step S113 the event determining unit 5 determines that the monitored person is sitting square.

Figure 15:
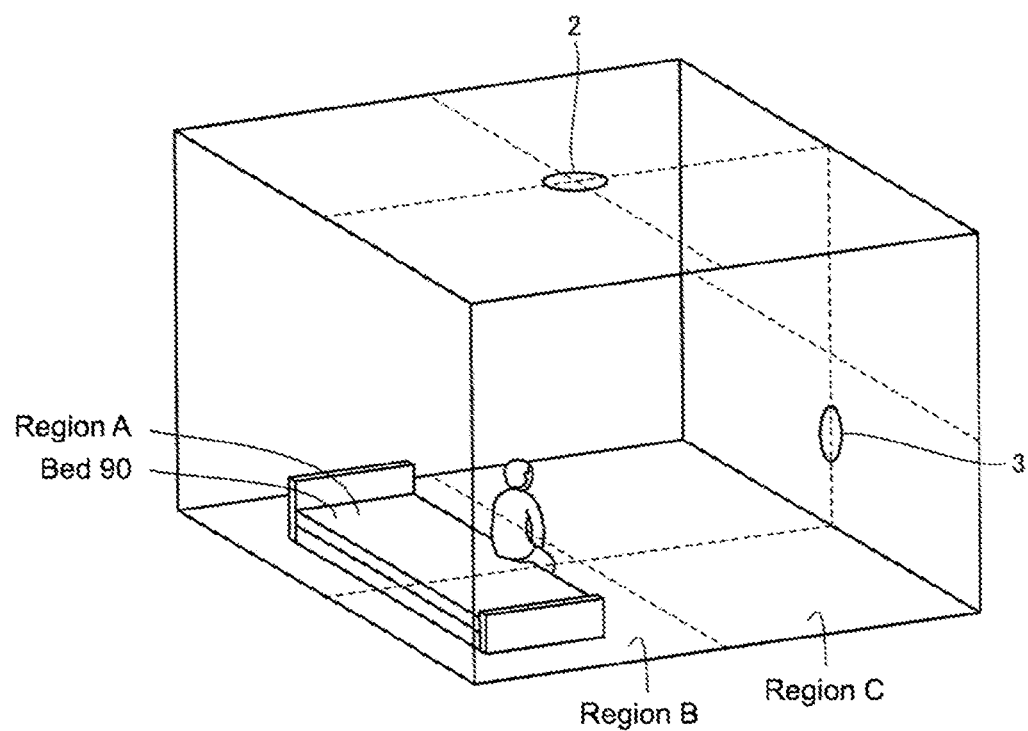
FIG. 15 illustrates the state of the monitored area when a monitored person is sitting square.
Figure 16:
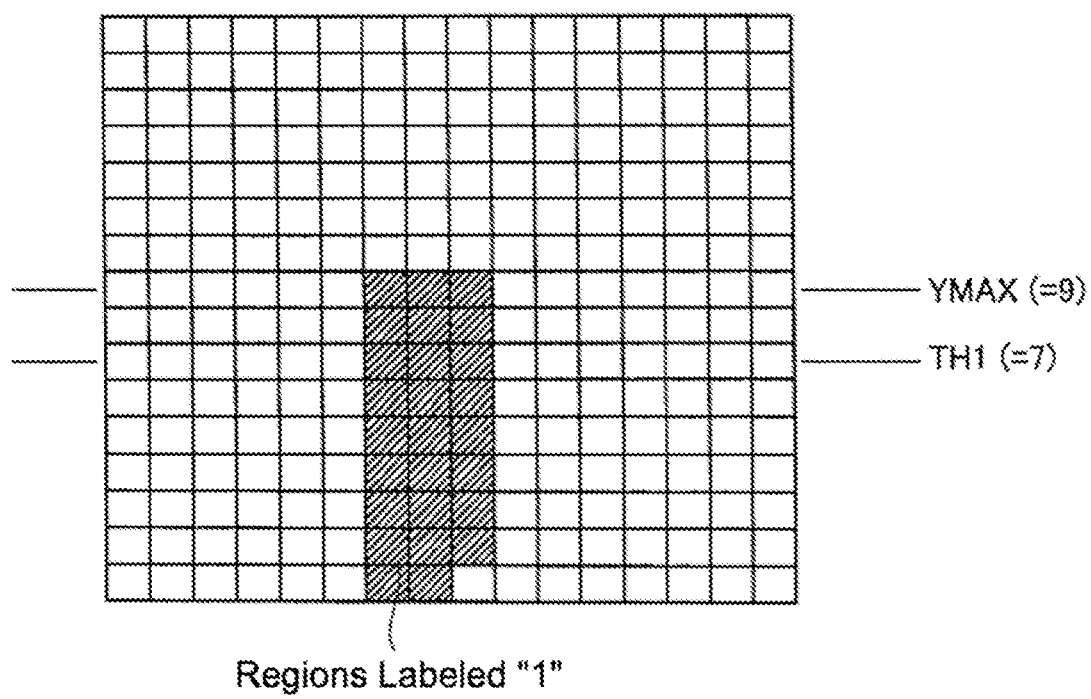
FIG. 16 illustrates a second labeled image data when the monitored area is in the state illustrated in FIG. 15.

FIG. 15 illustrates the state of the monitored area when a monitored person is sitting square. FIG. 16 illustrates a second labeled image data when the monitored area is in the state illustrated in FIG. 15. The maximum Y coordinate among the pixels in the region labeled "1" in the second labeled image data is "9". Given that the predetermined value TH1 is set to the value "7", the event determining unit determines that the monitored person is sitting square.

In step S114 the horizontal length detector 10 determines whether or not the horizontal length of the monitored person is greater than or equal to a reference value BA2 on the basis of the first labeled image data. In other words, the horizontal length detector 10 calculates the length D of the principal axis of a region labeled with "1" in the first labeled image data, i.e., the Euclidean distance between the ends of a line of maximum length that can be drawn between pixels in the region labeled with "1". Processing continues to step S115 when the horizontal length detector 10 determines that the length D of the principal axis is greater than or equal to the predetermined value TH2 corresponding to the reference value BA2, and terminates when the horizontal length detector 10 determines that the length D is less than the predetermined value TH2.

In step S115 the event determining unit 5 determines one type of fall event, namely, that the monitored person has fallen off the bed.

Figure 17:
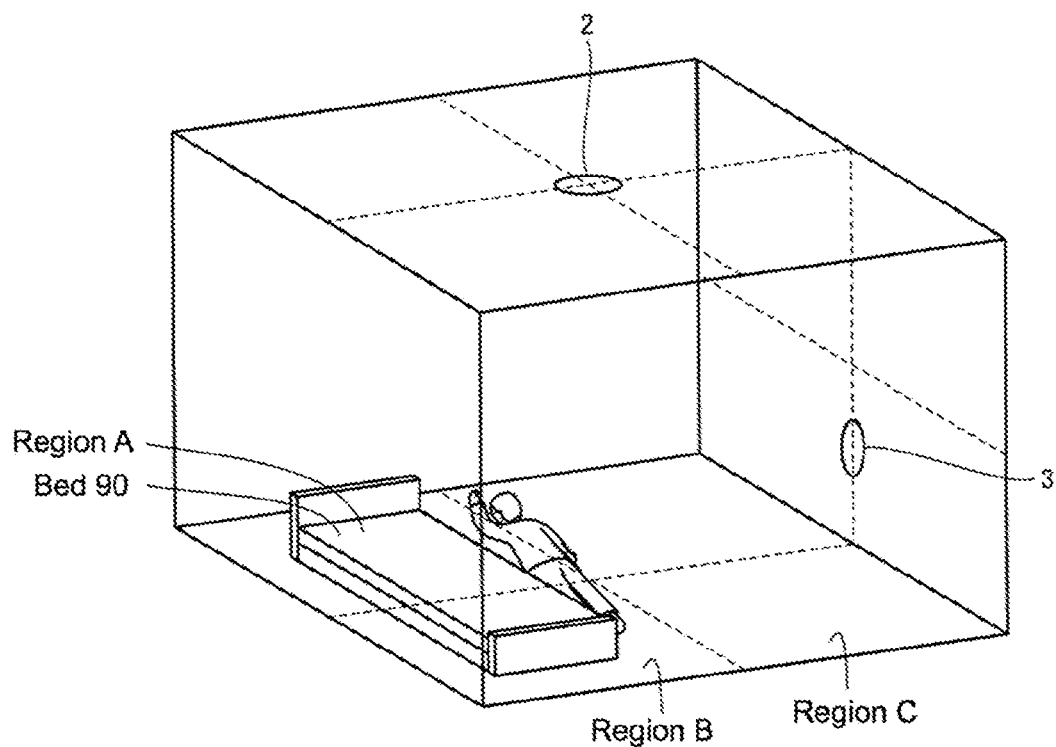
FIG. 17 illustrates the state of the monitored area when a monitored person has fallen.
Figure 18:
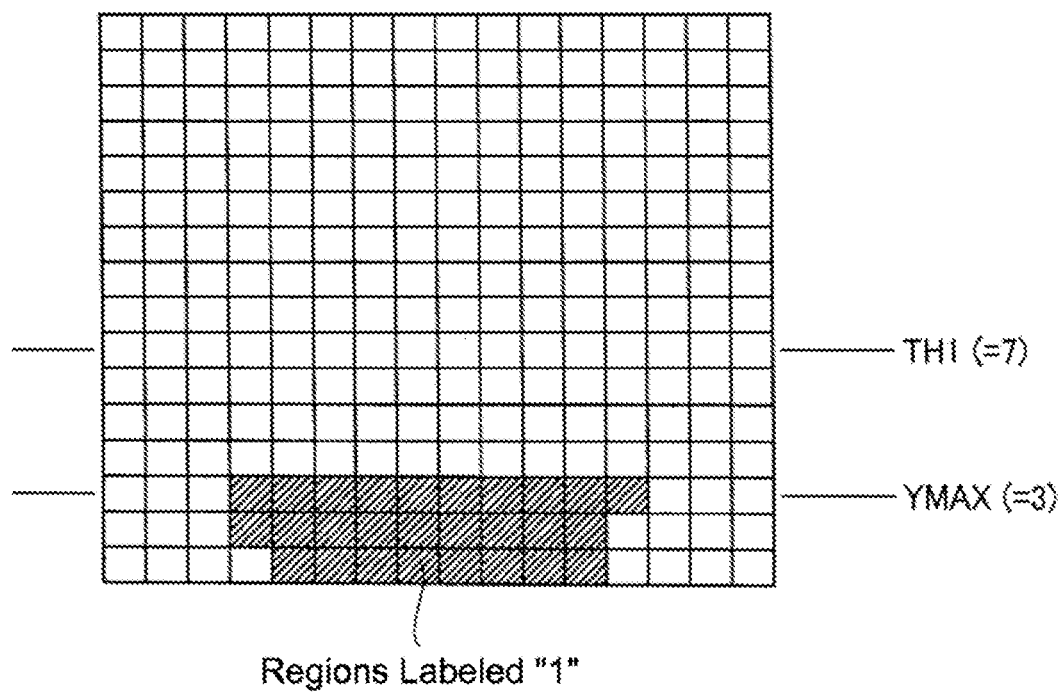
FIG. 18 illustrates a second labeled image data when the monitored area is in the state illustrated in FIG. 17.

FIG. 17 illustrates the state of the monitored area when a monitored person has fallen from a position. FIG. 18 illustrates a second labeled image data when the monitored area is in the state illustrated in FIG. 17. The maximum Y coordinate among the pixels in the region labeled with "1" in the second labeled image data is 3 and is less than the predetermined value TH1 which is 7.

Figure 19:
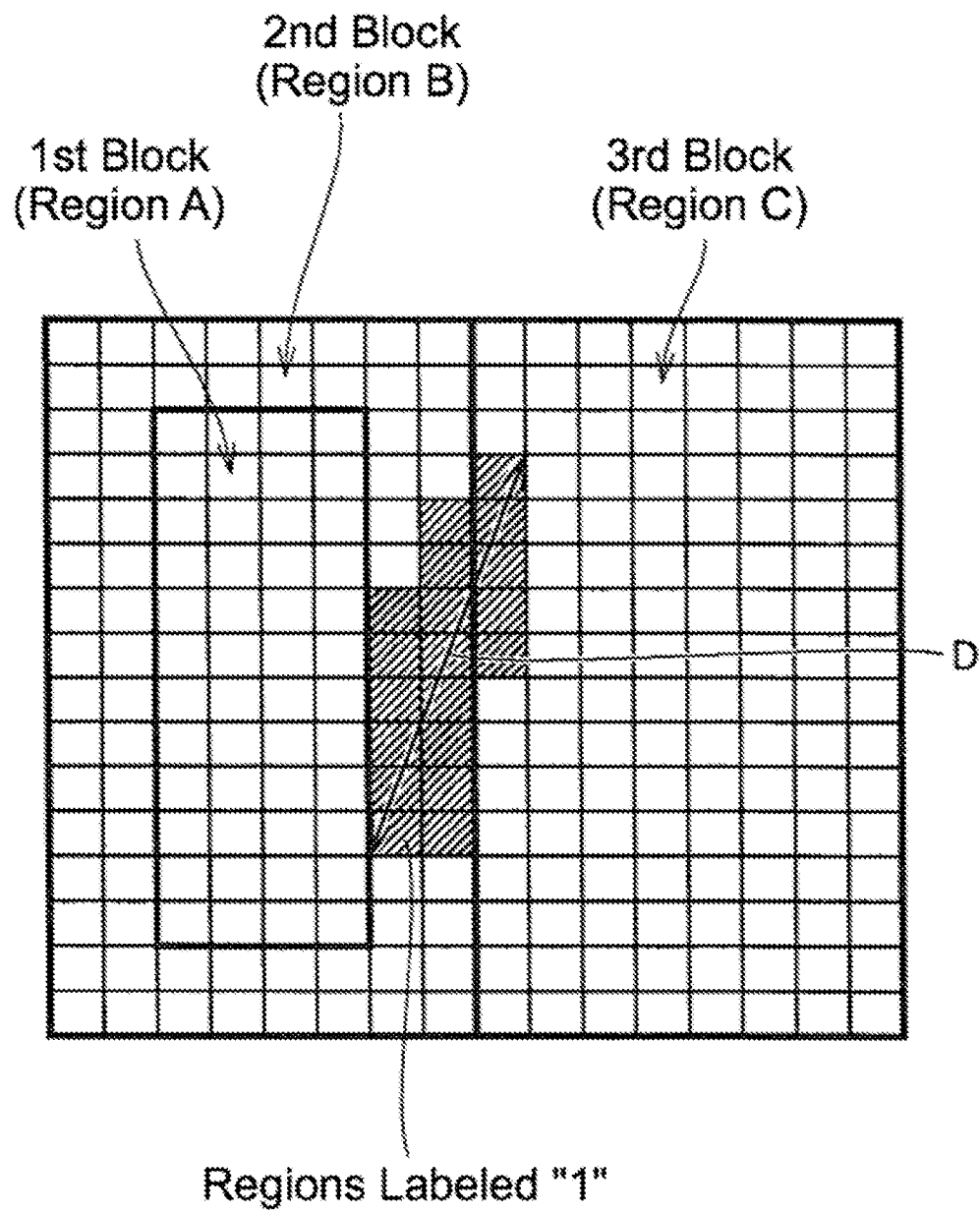
FIG. 19 illustrates a first labeled image data when the monitored area is in the state illustrated in FIG. 17.

FIG. 19 illustrates a first labeled of image data when the monitored area is in the state illustrated in FIG. 17.

The length D of the principal axis in the region labeled with "1" in the first labeled image data is 68½ and is greater than the predetermined value TH2, which is 7. Consequently, the event determining unit determines that the monitored person has fallen of the bed.

As above described, the embodiment is capable of detecting fall-related events of a monitored person even when there is a bed located in the monitored area, that is, the embodiment is capable of detecting that the monitored person has fallen, or detects the risk of the monitored person falling, such as when the monitored person is sitting legs outstretched in bed or is sitting square at the edge of the bed.

Second Embodiment

In the first embodiment, the monitoring device uses the first labeled image data to identify whether the monitored person is present in Region A (the bed area), Region B (the area surrounding the bed), or Region C (the regions excluding the bed area and the area surrounding the bed). In the second embodiment, the monitoring device uses a second labeled image to determine whether the monitored person is in the bed area, or is outside the bed area. This embodiment takes advantage of the fact that the lowest point on the monitored person is higher, and the length in the horizontal direction is longer when the monitored person is in the bed area than when the monitored person is outside the bed area.

Figure 20:
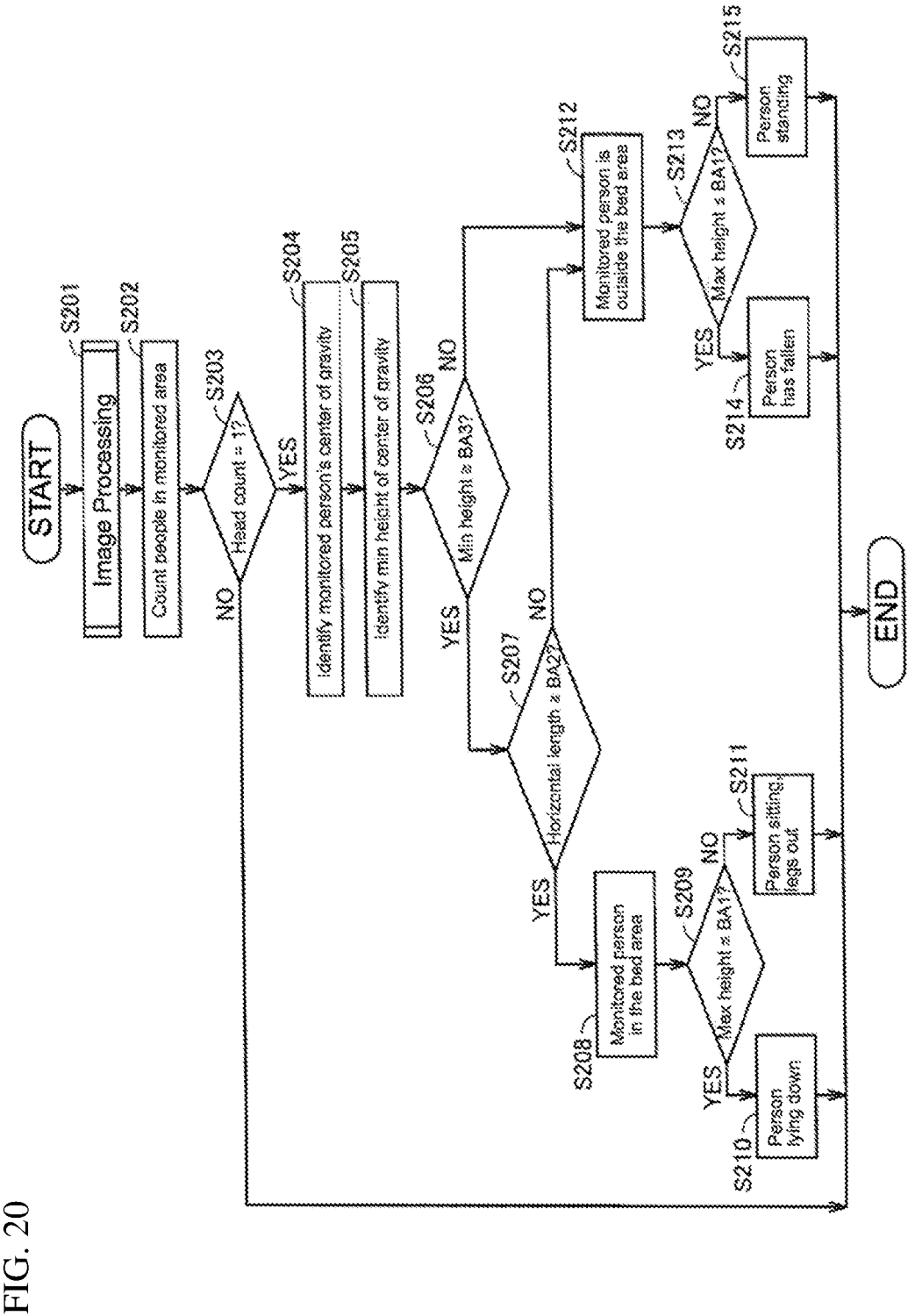
FIG. 20 is a flowchart of the procedures for assessing events related to a monitored person according to a second embodiment.

FIG. 20 is a flowchart of the procedures for assessing events related to a monitored person according to a second embodiment.

In step S201, the image processing unit 9 performs image processing according to the procedure depicted in FIG. 5 and thereby generates a first labeled image data and a second labeled image data from the first infrared image data output from the upper image sensor 2 and the second infrared image data output from the lateral image sensor 3.

In step S202, the head counting unit 6 identifies the number of people in the monitored area on the basis of the number of uninterrupted regions labeled with "1" in the first labeled image data. The head counting unit 6 determined there are N people in the monitored area when N uninterrupted regions in the first labeled image data are labeled with "1".

In step S203, the head counting unit 6 determines only the monitored person in the monitored area when only one person is present in the monitored area, and processing continues to step S204. When multiple people are in the monitored area, the head counting unit 6 determines that other persons are present in the monitored area besides the monitored person, e.g., an assistant or the like, and thus processing terminates.

In step S204, the horizontal-position identifying unit 7 determines the horizontal location of the center of gravity of the monitored person's physical body on the basis of the first labeled image data. In other words, the horizontal-position identifying unit 7 specifies the location of the pixels at the center of gravity in the region labeled with "1" in the first labeled image data.

In step S205, the vertical-position identifying unit 8 determines the lowest point of the monitored person's physical body on the basis of the second labeled image data. That is, the vertical-position identifying unit 8 corrects the region labeled with "1" in the second labeled image data on the basis of the location of the pixels at the center of gravity of the monitored person's physical body identified in step S204. The vertical-position identifying unit 8 identifies the minimum Y coordinate among the pixels corrected in the regions labeled with "1" in the second labeled image data.

In step S206, the vertical-position identifying unit 8 determines whether or not the lowest point on the physical body of the monitored person is greater than or equal to the reference value BA3 (FIG. 2) on the basis of the second labeled image data. That is, on determining that the identified minimum Y coordinate is greater than or equal to a predetermined value TH3 (FIG. 3) corresponding to the reference value BA3, the vertical-position identifying unit 8 determines that the monitored person may be in the bed area, and processing continues to step S207. Processing continues to step S212 when the vertical-position identifying unit 8 determines that the corrected minimum Y coordinate is less than the predetermined value TH3.

Figure 21:
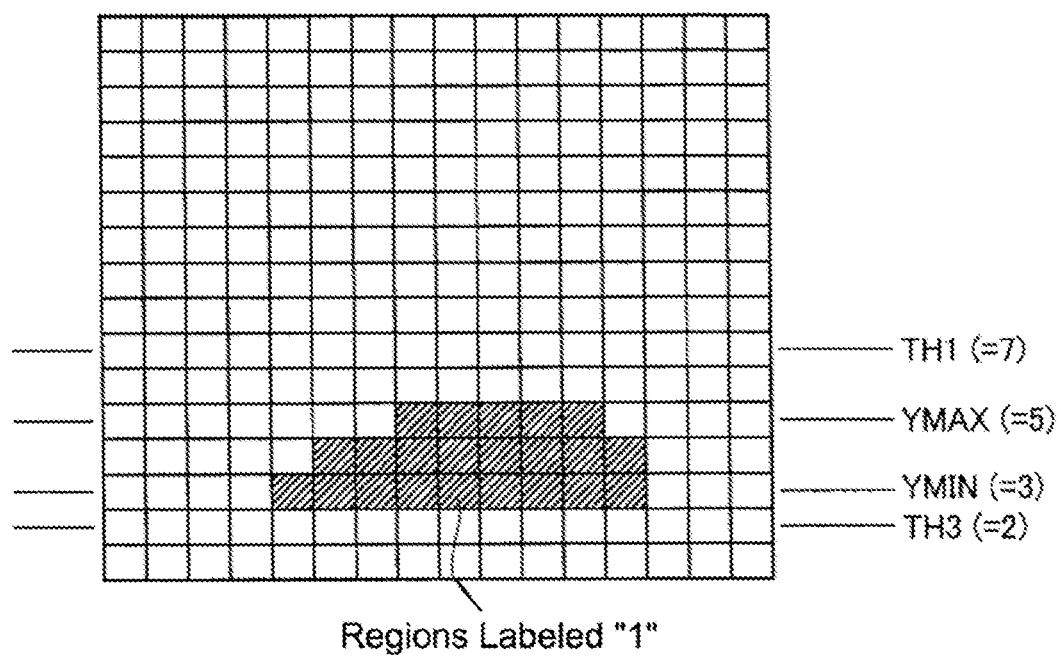
FIG. 21 illustrates a second labeled image data when a monitored person is in the bed area.

FIG. 21 depicts second labeled image data. The minimum Y coordinate among the pixels in the region labeled "1" in the second labeled image data is "3". Given that the predetermined value TH3 is set to the value "2", the system determines that the monitored person is in the bed area.

In step S207 the horizontal length detector 10 determines whether or not the horizontal length of the monitored person is greater than or equal to a reference value BA2 on the basis of the first labeled image data. In other words, the horizontal length detector 10 calculates the length D of the principal axis of a region labeled with "1" in the first labeled image data, i.e., the Euclidean distance between the ends of a line of maximum length that can be drawn between pixels in the region labeled with "1". Processing continues to step S208 when the horizontal length detector 10 determines that the length D of the principal axis is greater than or equal to the predetermined value TH2 corresponding to the reference value BA2, and continues to step S212 when the horizontal length detector 10 determines that the length D is less than the predetermined value TH2.

In step S208, the event determining unit 5 determines that the monitored person is in the bed area.

In step S209, the vertical-position identifying unit 8 determines whether or not the maximum height of the physical body of the monitored person is less than or equal to the reference value BA1 (FIG. 2) on the basis of the second labeled image data. The vertical-position identifying unit 8 identifies the maximum Y coordinate among the pixels corrected in the regions labeled with "1" in the second labeled image data in step S205. When the vertical-position identifying unit 8 determines that the identified maximum Y coordinate YMAX is less than or equal to a predetermined value TH1 (FIG. 3) corresponding to the reference value BA1, processing continues to step S210. Processing continues to step S211 when the vertical-position identifying unit 8 determines that the identified maximum Y coordinate YMAX exceeds the predetermined value TH1.

In step S210 the event determining unit 5 determines that the monitored person is lying down.

In step S211 the event determining unit 5 determines that the monitored person is sitting with legs outstretched.

In step S212, the system determines that the monitored person is outside in the bed area.

In step S213, the vertical-position identifying unit 8 determines whether or not the maximum height of the physical body of the monitored person is less than or equal to the reference value BA1 (FIG. 2) on the basis of the second labeled image data. The vertical-position identifying unit 8 identifies the maximum Y coordinate among the pixels corrected in the regions labeled with "1" in the second labeled image data in step S205. When the vertical-position identifying unit 8 determines that the identified maximum Y coordinate YMAX is less than or equal to a predetermined value TH1 (FIG. 3) corresponding to the reference value BA1, processing continues to step S214. Processing continues to step S215 when the vertical-position identifying unit 8 determines that the identified maximum Y coordinate YMAX exceeds the predetermined value TH1.

In step S214 the event determining unit 5 determines that the monitored person has fallen.

In step S215 the event determining unit 5 determines that the monitored person is standing.

As above described, a monitoring device according the embodiment is capable of detecting whether or not a monitored person is in the area where a bed is present even with a bed located in the monitored area and even without knowing in advance the area where the bed is present. The monitoring device according to the embodiment is able to detect the monitored person lying down or sitting with legs outstretched in an area where a bed is present, and is able to detect that the monitored person has fallen down or is standing in an area where no bed is present.

Note that in the embodiment, although in step S207 it is determined after a determination of YES at step S206 whether or not the length of the monitored person in the horizontal direction is greater than or equal to the reference value BA2 on the basis of the first labeled image data, step S207 may be omitted.

All aspects of the embodiments disclosed should be considered merely examples and not limitations as such. The scope of the present invention is not limited to the above description but to the scope of the claims, and is intended to include all equivalents and modifications allowable by the scope of the claims.

REFERENCE NUMERALS

1 Monitoring system
2 Upper image sensor
3 Lateral image sensor
4 Position identifying unit
5 Event determining unit
6 Head counting unit
7 Horizontal-position identifying unit
8 Vertical-position identifying unit
9 Image processing unit
10 Horizontal length detector
20 Monitoring device
21 Display unit

The invention claimed is:

1. A monitoring device comprising a processor configured with a program to perform operations comprising:
   operation as a position identifying unit configured to identify:
      a horizontal location of a monitored person in a monitored area comprising a bed, based on top-down image data acquired by a first image sensor provided above the monitored area capturing a first image of the monitored area; and
      a height of the monitored person based on lateral image data acquired by a second image sensor provided along a side of the monitored area capturing a second image of the monitored area; and
   operation as an event determining unit configured to determine whether a fall-related event for the monitored person has occurred based on the horizontal location of the monitored person and a maximum value of the height of the monitored person, wherein
   the horizontal location of the monitored person comprises a location of the monitored person on a horizontal plane of a three-dimensional area of the monitored area, the horizontal plane oriented substantially perpendicular to a direction of the height of the monitored person,
   the monitored area comprises a first horizontal region, a second horizontal region that surrounds the first horizontal region, and a third horizontal region that excludes the first horizontal region and the second horizontal region, the third horizontal region excluding the bed and an area surrounding the bed,
   the processor is configured with the program to perform operations such that operation as the event determining unit comprises operation as the event determining unit that determines a fall event has occurred in response to the position identifying unit identifying that the horizontal location of the monitored person is in the third horizontal region and that the maximum height of the monitored person in the third horizontal region is less than or equal to a first predetermined value, and
   the processor is configured with the program to perform operations such that operation as the position identifying unit comprises operation as the position identifying unit that is configured to use the top-down image data acquired by the first image sensor capturing an image of the monitored area to identify a number of people in the monitored area, and to only identify the horizontal location of the monitored person and the maximum value of the height of the monitored person in response to determining that there is only one person in the monitored area.

2. The monitoring device according to claim 1, wherein the processor is configured with the program to perform operations such that operation as the event determining unit comprises operation as the event determining unit that determines that the monitored person is lying down in response to the monitored person being located in the first horizontal region and the maximum value of the height of the monitored person being less than or equal to the first predetermined value.

3. The monitoring device according to claim 2, wherein the processor is configured with the program to perform operations such that operation as the event determining unit comprises operation as the event determining unit that determines that the monitored person is sitting legs outstretched in response to the monitored person being located in the first horizontal region and the maximum value of the height of the monitored person exceeding the first predetermined value.

4. The monitoring device according to claim 2, wherein the processor is configured with the program to perform operations such that operation as the event determining unit comprises operation as the event determining unit that determines that the monitored person is sitting square in response to the monitored person being located in the second horizontal region and the maximum value of the height of the monitored person being greater than or equal to the first predetermined value.

5. The monitoring device according to claim 4, wherein the monitored area comprises a space where the monitored person resides, and the first horizontal region contains the bed.

6. The monitoring device according to claim 5, wherein the processor is configured with the program to perform operations such that:
   operation as the position identifying unit comprises operation as the position identifying unit that uses the top-down image data to calculate a horizontal length of the monitored person; and
   operation as the event determining unit comprises operation as the event determining unit that determines that the monitored person has fallen from the bed in response to the monitored person being located in the second horizontal region, the maximum value of the height of the monitored person being less than or equal to the first predetermined value, and the horizontal length of the monitored person being greater than or equal to a second predetermined value.

7. The monitoring device according to claim 4, wherein the processor is configured with the program to perform operations such that operation as the event determining unit comprises operation as the event determining unit that determines that the monitored person is standing in response to the monitored person being in the third horizontal region and the maximum value of the height of the monitored person exceeding the first predetermined value.

8. The monitoring device according to claim 1, wherein the processor is configured with the program to perform operations such that:
   operation as the position identifying unit comprises operation as the position identifying unit that identifies a minimum value of the height of the monitored person based on the lateral image data; and
   operation as the event determining unit comprises operation as the event determining unit that determines that the monitored person is in an area containing the bed in response to the minimum value of the height of the monitored person being greater than or equal to a third predetermined value.

9. A monitoring system comprising:
   a first image sensor provided above a monitored area comprising a bed;
   a second image sensor provided along a side of the monitored area; and
   a processor configured with a program to perform operations comprising:
      operation as a position identifying unit configured to identify:
         a horizontal location of a monitored person based on top-down image data acquired by the first image sensor provided above a monitored area capturing a first image of the monitored area; and a height of the monitored person based on lateral image data acquired by the second image sensor capturing a second image of the monitored area; and operation as an event determining unit configured to determine whether a fall-related event for the monitored person has occurred based on the horizontal location of the monitored person and a maximum value of the height of the monitored person, wherein the horizontal location of the monitored person comprises a location of the monitored person on a horizontal plane of a three-dimensional area of the monitored area, the horizontal plane oriented substantially perpendicular to a direction of the height of the monitored person, the monitored area comprises a first horizontal region, a second horizontal region that surrounds the first horizontal region, and a third horizontal region that excludes the first horizontal region and the second horizontal region, the third horizontal region excluding the bed and an area surrounding the bed, the processor is configured with the program to perform operations such that operation as the event determining unit comprises operation as the event determining unit that determines a fall event has occurred in response to the position identifying unit identifying that the horizontal location of the monitored person is in the third horizontal region and that the maximum height of the monitored person in the third horizontal region is less than or equal to a first predetermined value, and the processor is configured with the program to perform operations such that operation as the position identifying unit comprises operation as the position identifying unit that is configured to use the top-down image data acquired by the first image sensor capturing an image of the monitored area to identify a number of people in the monitored area, and to only identify the horizontal location of the monitored person and the maximum value of the height of the monitored person in response to determining that there is only one person in the monitored area.

10. A non-transitory computer-readable medium storing a monitoring program that, when read and executed, causes a computer to perform operations comprising:

operation as a position identifying unit configured to identify:
  a horizontal location of a monitored person based on top-down image data acquired by a first image sensor provided above a monitored area comprising a bed, the first image sensor capturing a first image of the monitored area; and
  a height of the monitored person based on lateral image data acquired by a second image sensor provided along a side of the monitored area capturing a second image of the monitored area; and operation as an event determining unit configured to determine whether a fall-related event for the monitored person has occurred based on the horizontal location of the monitored person and a maximum value of the corrected height of the monitored person, wherein the horizontal location of the monitored person comprises a location of the monitored person on a horizontal plane of a three-dimensional area of the monitored area, the horizontal plane oriented substantially perpendicular to a direction of the height of the monitored person the monitored area comprises a first horizontal region, a second horizontal region that surrounds the first horizontal region, and a third horizontal region that excludes the first horizontal region and the second horizontal region, the third horizontal region excluding the bed and an area surrounding the bed, and operation as the event determining unit comprises operation as the event determining unit that determines a fall event has occurred in response to the position identifying unit identifying that the horizontal location of the monitored person is in the third horizontal region and that the maximum height of the monitored person in the third horizontal region is less than or equal to a first predetermined value, and operation as the position identifying unit comprises operation as the position identifying unit that is configured to use the top-down image data acquired by the first image sensor capturing an image of the monitored area to identify a number of people in the monitored area, and to only identify the horizontal location of the monitored person and the maximum value of the height of the monitored person in response to determining that there is only one person in the monitored area.

* * * * *